United States Patent
Goldbach (10) Patent No.: US 7,444,178 B2
(45) Date of Patent: Oct. 28, 2008

(54) POSITIONAL MARKER SYSTEM WITH POINT LIGHT SOURCES

(75) Inventor: Günter Goldbach, Forstinning (DE)

(73) Assignee: BrainLAB AG, Feldkirchen (DE)

( * ) Notice: Subject to any disclaimer, the term of this patent is extended or adjusted under 35 U.S.C. 154(b) by 237 days.

(21) Appl. No.: 11/244,437

(22) Filed: Oct. 5, 2005

(65) Prior Publication Data
US 2006/0082789 A1 Apr. 20, 2006

Related U.S. Application Data (60) Provisional application No. 60/619,352, filed on Oct. 14, 2004.

(30) Foreign Application Priority Data
Oct. 5, 2004 (EP) ............................. 04023718.2

(51) Int. Cl.
*A61B 8/12* (2006.01)
*A61N 5/00* (2006.01)
*G06T 7/20* (2006.01)

(52) U.S. Cl. ............................. 600/427; 600/3; 600/424; 382/103; 382/107

(58) Field of Classification Search ................ 356/614, 356/620, 625; 600/425–430, 3, 439; 250/203.1, 250/206.1; 128/665, 653.1, 653.2; 382/103, 382/106–107, 154, 291, 304
See application file for complete search history.

(56) References Cited

U.S. PATENT DOCUMENTS

| | | | |
|---|---|---|---|
| 4,070,116 A * | 1/1978 | Frosch et al. | 356/625 |
| 5,197,476 A | 3/1993 | Nowacki et al. | |
| 5,383,454 A | 1/1995 | Bucholz | |
| 5,662,111 A * | 9/1997 | Cosman | 600/417 |
| 5,828,770 A | 10/1998 | Leis et al. | |
| 5,831,735 A | 11/1998 | Corby, Jr. | |
| 5,834,759 A * | 11/1998 | Glossop | 250/203.1 |
| 5,921,992 A | 7/1999 | Costales et al. | |
| 5,928,140 A | 7/1999 | Hardten | |
| 6,006,126 A * | 12/1999 | Cosman | 600/426 |
| 6,026,315 A * | 2/2000 | Lenz et al. | 600/414 |
| 6,275,725 B1 * | 8/2001 | Cosman | 600/426 |

(Continued)

FOREIGN PATENT DOCUMENTS

DE    196 39 615 A1    4/1998

(Continued)

OTHER PUBLICATIONS

Günter Goldbach, Tracking System With Scattering Effect Utilization, in Particular With Star Effect and/or Cross Effect Utilization, U.S. Appl. No. 11/244,662, filed Oct. 5, 2005.

(Continued)

*Primary Examiner*—Sang Nguyen
(74) *Attorney, Agent, or Firm*—Renner, Otto, Boisselle & Sklar, LLP (57) ABSTRACT

A positional marker system is disclosed. The positional marker system includes at least one light-emitting or light-reflecting marker that can be positionally detected by an optical tracking system, such as a medical tracking system, wherein the emitting and/or reflecting portion of the marker or markers is formed as a point light source and/or point light reflector.

13 Claims, 5 Drawing Sheets

U.S. PATENT DOCUMENTS

| | | | |
|---|---|---|---|
| 6,288,785 B1 * | 9/2001 | Frantz et al. | 356/614 |
| 6,324,296 B1 * | 11/2001 | McSheery et al. | 382/107 |
| 6,351,659 B1 | 2/2002 | Vilsmeier | |
| 6,381,485 B1 * | 4/2002 | Hunter et al. | 600/407 |
| 6,405,072 B1 * | 6/2002 | Cosman | 600/426 |
| 6,437,820 B1 | 8/2002 | Josefsson | |
| 6,484,049 B1 | 11/2002 | Seeley | |
| 6,490,475 B1 | 12/2002 | Seeley | |
| 6,491,699 B1 * | 12/2002 | Henderson et al. | 606/130 |
| 6,493,095 B1 | 12/2002 | Song et al. | |
| 6,584,339 B2 * | 6/2003 | Galloway et al. | 600/426 |
| 6,675,040 B1 * | 1/2004 | Cosman | 600/427 |
| 6,782,287 B2 * | 8/2004 | Grzeszczuk et al. | 600/424 |
| 6,978,167 B2 * | 12/2005 | Dekel et al. | 600/426 |
| 7,043,961 B2 * | 5/2006 | Pandey et al. | 73/1.81 |
| 7,125,419 B2 * | 10/2006 | Sequin et al. | 623/1.35 |
| 7,139,418 B2 * | 11/2006 | Abovitz et al. | 382/132 |
| 7,333,202 B2 * | 2/2008 | Birlem | 356/429 |
| 2002/0051255 A1 * | 5/2002 | Mooty et al. | 358/509 |
| 2002/0095081 A1 | 7/2002 | Vilsmeier | |
| 2003/0099435 A1 | 5/2003 | Yang | |
| 2003/0174401 A1 | 9/2003 | Brunner et al. | |
| 2003/0181800 A1 | 9/2003 | Bonutti | |
| 2003/0225329 A1 | 12/2003 | Rossner et al. | |
| 2004/0015075 A1 * | 1/2004 | Kimchy et al. | 600/424 |
| 2004/0122311 A1 | 6/2004 | Cosman | |
| 2006/0089552 A1 * | 4/2006 | Goldbach | 600/439 |

FOREIGN PATENT DOCUMENTS

| | | |
|---|---|---|
| DE | 10 056 186 A1 | 5/2002 |
| WO | 97/47240 | 12/1997 |
| WO | 00/16121 | 3/2000 |
| WO | 03/038481 A1 | 5/2003 |
| WO | 2004/078039 A1 | 9/2004 |

OTHER PUBLICATIONS

European Search Report for corresponding Application No. 04023718.2 dated Mar. 11, 2005.

* cited by examiner

POSITIONAL MARKER SYSTEM WITH POINT LIGHT SOURCES

RELATED APPLICATION DATA

This application claims priority of U.S. Provisional Application No. 60/619,352 filed on Oct. 14, 2004, which is incorporated herein by reference in its entirety.

FIELD OF THE INVENTION

The invention relates to a positional marker system and, more particularly, to a positional marker system that includes at least one light-emitting or light-reflecting marker that can be positionally detected by an optical tracking system.

BACKGROUND OF THE INVENTION

Positional marker systems for optical tracking systems and, in particular, medical tracking systems, are known in principle. For example, a reflector or reflective referencing system is known from DE 19 639 615 C2 (U.S. Pat. No. 6,351,659 B1), wherein the positional markers are formed as passive markers and include spheres with a reflective covering or coating. Optical radiation reflected off of these spheres can be detected by a camera-assisted tracking system, and their spatial position can be determined. Instruments, patients or treatment apparatus coupled to the spheres can be spatially detected and tracked, thereby providing a surgeon visual assistance during surgery.

Further, active markers are known that function in a similar manner as passive markers, but are powered by power sources such as batteries or power packs. Active markers are light emitting devices, such devices being known, for example, from U.S. Pat. No. 5,197,476. U.S. Pat. No. 5,383,454 and U.S. Pat. No. 5,831,735 also show examples of non-contact, optical tracking with the aid of positional markers.

A disadvantage of previously known, active markers such as, for example, LED markers, is the relatively large dimensions of the markers and/or the active or emitting portion of the markers. More specifically, the markers take up a relatively large space and are difficult to attach to smaller or very thin objects. Also, LEDs provide a very non-homogeneous light pattern.

As for the passive markers, the problem arises that they have to be relatively large in order to be detected by the cameras. Relatively large markers, however, can become partially covered or tarnished while being used, or, due to manufacturing tolerances, can exhibit a shape which is not entirely regular. In the case of such passive markers, their center, which precisely reproduces the location of the marker, can be ascertained by calculating a "focus". The focus can be determined by analyzing a projected external shape of the marker and calculating a center point. If the markers are partially covered, tarnished or of different sizes, however, it may not be possible to precisely calculate the center point. Errors arise, which, in applications that demand a high degree of accuracy (e.g., surgical applications) are undesirable. Also, if a marker becomes tarnished or covered, for example, recording the marker from two different cameras (e.g., two cameras having different perspective views of the marker) may produce recordings having different shapes. The same applies to active markers (e.g., LEDs) since they have non-homogeneous emissions.

SUMMARY OF THE INVENTION

As used herein, the term "point light source" includes light sources having very small dimensions, whose position can be precisely determined on a camera sensor, and whose brightness is sufficient to expose the sensor.

The emitting and/or reflecting portion of the marker or markers discussed above shall also be referred herein as a "point light". These point lights can emit or reflect a homogenous light in an emitting direction. In other words, a point light outputs the same image from all directions of its illuminating range.

One way of defining the size of the point lights, i.e., the size of the actually emitting and/or reflecting portion of the marker or markers, is to define the size via its positioning tolerance (positioning accuracy). In the field of optical tracking systems, a positioning tolerance or positioning accuracy can be defined as the accuracy in determining a spatial position of markers (in most cases, relative to each other, but also absolutely). The point lights preferably have a size which is less than 25 times their positioning tolerance.

The point lights, for example, can have a maximum size of about 3 millimeters (mm), more preferably about 2 mm, and even more preferably about 1 mm or a fraction of 1 mm. Furthermore, the point lights, for example, can have a minimum size of about 30 micrometers ($\mu$m), more preferably about 50 $\mu$m, and even more preferably about 62.5 $\mu$m.

A positional marker system is preferably configured such that the point light or point lights can be processed and/or formed such that they emit or reflect light in a spatially uniform distribution. In one embodiment, for example, the end of a photoconductive inner part of an optical fiber is polished or burnished such that it forms a convex scattering lens.

In accordance with a preferred embodiment of the positional marker system, the marker system includes a number of markers that are the ends of optical fibers fed from a common light source, wherein the light source can be an actively emitting source or a light collecting device that collects ambient light.

In another embodiment, the point lights can be reflector markers manufactured from a material that exhibits a refraction index of up to 2.4 or 2.6, such as a diamond, rutile, fabulite, moissanite material, or the like.

In accordance with another embodiment, the point light or point lights can be reflector markers made of a transparent or semi-transparent material that exhibits a crystal cut or diamond cut, such as an ideal cut, for example.

The forgoing and other embodiments of the invention are hereinafter discussed with reference to the drawings.

DETAILED DESCRIPTION

Figure 1A:
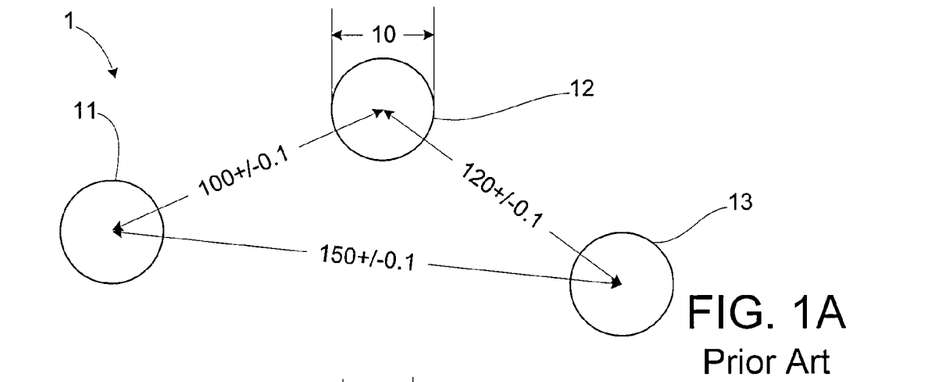
FIGS. 1A and 1B are schematic diagrams illustrating a comparison of a size of conventional reflector markers and point light markers.
Figure 1B:
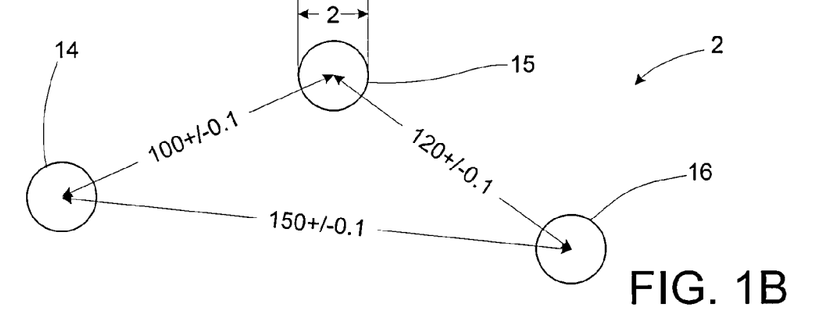

FIGS. 1A and 1B show a contrast between a conventional positional marker system 1 (FIG. 1A) and a positional marker system 2 (FIG. 1B) in accordance with the invention. The markers of the conventional system 1 are the actual reflecting surface of a reflector marker 11, 12, 13. Usually, spherical or discoid retro-reflecting surfaces are used that reflect light in an output direction over a relatively large area. This generates a projection of the marker within the tracking system. Three such markers, for example, can be attached to a patient's body part or on a rigid body (marker geometry), in order to ascertain a spatial position of the markers via a tracking system. The markers 11, 12 and 13 of the conventional marker system 1 exhibit different center-to-center distances from each other, such as, for example, 100, 120 and 150 mm, and they have a diameter of 10 mm. The positioning tolerance or positioning accuracy, e.g., the accuracy in determining the spatial position of individual markers (relative to each other, but also absolutely), is given here to ±0.1 mm. This is a typical positioning tolerance.

The markers 14, 15, 16 of the positional marker system 2 in accordance with the invention are configured to be much smaller than conventional markers, wherein the reflecting surface of the markers can be substantially smaller than conventional markers. Retro-reflecting surfaces for enlarging the effective marker surface are therefore not required. In the present case, the markers have a diameter of only 2 mm. Given the same positioning tolerance and the same distances from each other, this roughly corresponds to 20 times the positioning tolerance.

Using point light source markers results in two-dimensional positions being measured more precisely (using a camera), and, when using a stereoscopic camera system, increases the three-dimensional detection accuracy of the system. This is due to the fact that a point light source marker outputs the same image from two directions with a greater probability than a relatively large marker, since mechanical deforming, covering and a non-uniform brightness distribution can be eliminated by simple means and, therefore, no longer influence interpolating the position.

The point light source markers, configured as individual illuminating objects, have a series of advantages. For example, the potential error when calculating or estimating the center point (focus) is in principle reduced or eliminated. Further, the risk of markers being partially hidden and, therefore, incorrectly estimating the focus, is limited because the markers are either completely covered or not covered at all. If a marker is completely covered, this need not result in a system failure since more than the required minimum number of markers for locating a single object can in principle be provided. Additionally, after a certain period of time a marker will no longer be covered, such that locating the object can be accurately ascertained. In medical applications, such as when tracking surgical instruments, the size of potential covering objects (e.g., blood, water droplets, surgeon's fingers, etc.) typically will be larger than that of the point light marker. This ensures that a marker, which may be partially visible, is not incorrectly detected such that the determined position as a whole is distorted. Other advantages relate to the lower weight of instruments provided with such small markers and the possibility of integrating markers into very thin instruments, for example into catheters, drilling tools, etc.

The positional marker system can be an active or passive marker system, e.g., can comprise point light sources that emit light themselves or which merely reflect light. Furthermore, active systems, e.g., systems having markers that emit light, can include different light sources within the framework of the invention. Light sources can be provided that have their own power supply, e.g., a light source which is fed by a battery, a power pack, a fuel cell, a solar cell, or the like, provided in a cable-free instrument to be located by means of the point light sources. A fiber optic cable also can be connected to the positional marker light supply using an internal or an external power supply for the light source.

Figures 2, 3, 4:
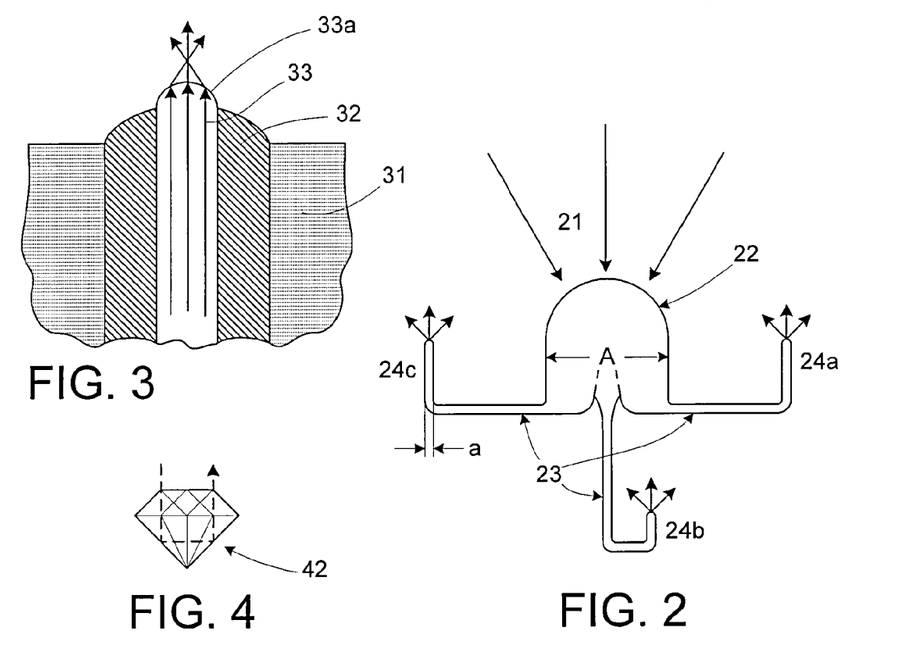
FIG. 2 illustrates an optical fiber array with a light collecting device in accordance with an embodiment of the invention.
FIG. 3 illustrates the end of an optical fiber with a point light source.
FIG. 4 illustrates a marker reflector having a diamond cut.
Figure 5A:
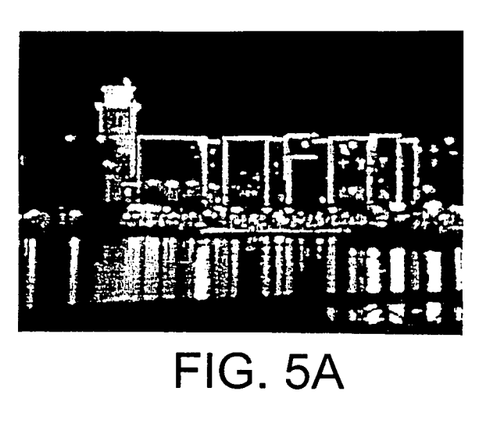
FIGS. 5A-5B and 6A-6B illustrate examples of images with and without star and/or cross effects.
Figure 5B:
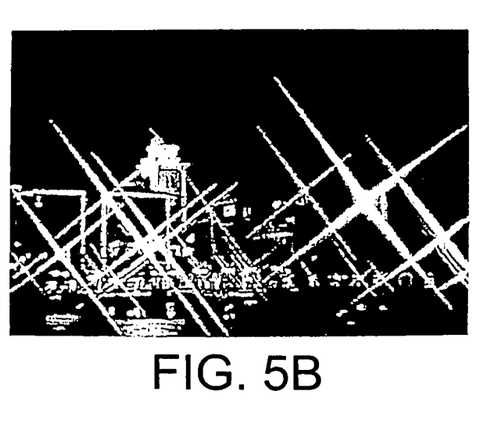
Figure 6A:
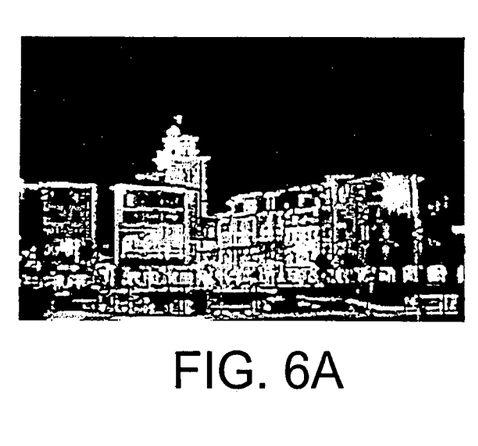
Figure 6B:
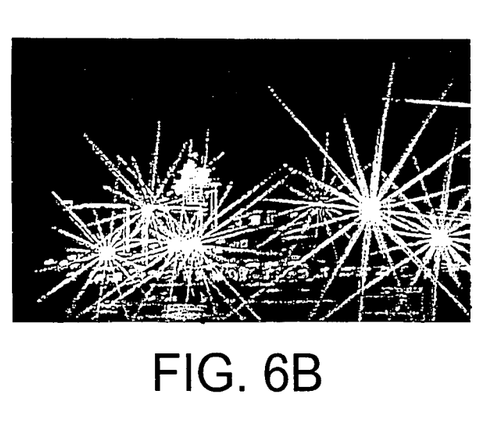

In one embodiment, a cable-free object, e.g., a surgical instrument, can be provided that can operate without an independent or external (e.g., electrical) power supply and which nonetheless exhibits a very high energy density of the positional marker point lights. A positional marker system for such a surgical instrument (or for surgical treatment apparatus and/or for marking patient's body parts) includes a light collecting device from which at least one optical fiber extends, the end of which forms a point light source. FIG. 2 schematically shows such an arrangement. External light 21, e.g., ambient light or light from an active light source (e.g., a constantly illuminating or intermittent light source) is collected in a relatively large collimator lens 22. In the case of medical applications, the light collecting lens 22 can be positioned at the rear or back portion of an instrument. The light collecting lens 22 can be amply supplied with visible light by surgical lights, preferably bright surgical lights, or by a separate light source that emits or reflects invisible light and/or invisible electromagnetic radiation (e.g., ultraviolet or infrared). The collimator lens 22 can be constructed such that it splits into a number of small optical fibers 23 that transport the light collected by the lens 22 to the precisely positioned point light sources 24a to 24c. The optical fibers 23 can be manufactured from a flexible or rigid plastic material or a glass material having optimized light transmission properties, such as is known from optical glass fiber data transmission lines. The brightness of the light emitted or reflected at the ends and/or the point light sources 24a to 24c is a function of the size (measurement A) of the collimator lens 22 with respect to the aperture of the point light sources 24a to 24c (measurement a), the number of optical fibers used, and the optical properties of the material used.

Based on this principle, a relatively bright point light marker can be achieved by passive illumination. As the aperture (a) is reduced in size, the light density at the ends 24a to 24c is increased. Stronger ambient light results in a higher marker brightness and therefore provides a good signal-to-noise ratio over a wide range of properties of the incident light.

As indicated above, one way of manufacturing active point light markers having a very small size is to use conventionally available fiber optic cables made of glass, plastic, or the like, such as are used, for example, in telecommunications. The photoconductive inner part of a glass fiber array typically may have a size of 50 to 62.5 μm for multi-mode fibers. Optical plastic fibers are available with diameters of up to a few millimeters. The light intensity from a laser or an LED light source introduced into such a fiber is known or can be ascertained.

FIG. 3 shows one way of configuring a point light source using an optical fiber. The optical fiber 33 itself is typically surrounded by a jacket 32, which is in turn anchored in the object to be provided with the point light source, e.g., in a wall 31 of a surgical instrument. At its end 33a, the optical fiber 33 protrudes slightly out of the jacket 32. In the embodiment shown, the end 33a is polished or burnished and thus forms a convex distributor lens which outputs the light uniformly in all emitting directions.

Another way of uniformly distributing the light at the end of the fiber, for example, is to make the end of the glass or plastic fiber dispersive by implanting or placing small particles in the surface of the fiber, or by uniformly attaching recesses or grooves to the facing side of the fiber.

In another embodiment, there is provided passive point light reflectors. An advantage of such point light reflectors is that they do not require a light or a power supply and, therefore, the structures are much simpler to fabricate. Point light reflectors can be provided that can deliver a high degree of retro-reflection, and this can be enabled, for example, by using materials that exhibit a high refraction index. Such materials include, for example, diamond, rutile, fabulite, moissanite materials, or the like, which exhibit a refraction index on the order of 2.4 to 2.6. The effect is known as the "diamond effect". For materials having a high refraction index, the angle for total reflection (total inner reflection) is on the order of 24 degrees. As a result, the incident light is reflected at an extremely broad range of illumination angles.

In order to use incident light from a direction other than the viewing direction, it also is possible to use specific geometric shapes for the crystals to generate a bright light effect (e.g., a spotlight effect). This can greatly simplify the setup for a number of applications in which positional measurements are restricted by camera systems having a small size, low weight and simple handling. The marker 42 in FIG. 4 shows the classic diamond cut such as can be used to generate highly reflective effects.

Very small markers (e.g., crystals, diamonds) on the order of a fraction of a millimeter can be used and, therefore, it is not necessary to use large crystals or large crystal arrays. Such highly reflective passive point light source markers enable costs to be greatly reduced, add very little weight, and can be introduced into very small objects.

Polished or tempered metal or plastic spheres, which can be small when compared to established marker systems (see FIG. 1B), represent another embodiment of the point light source markers. An advantage of using metal or plastic spheres is the new marker technology can be adapted to a number of instruments (e.g., surgical instruments) already in use. Other advantages are cost-effective mass production and an increased durability of the markers as compared to established markers (in particular, as compared to retro-reflective surfaces).

The invention can be used or combined with an image generating device for an optical tracking system, in particular a medical tracking system, for determining the position of a recorded image point.

In most cases, known optical tracking systems and their image generating devices include a pair of cameras that record individual image points, such as positional markers or natural landmarks, and detect information on position (e.g., the spatial position of the image points) from a stereoscopic image. Thus, there are systems that already include an image processing unit in the camera system and provide the spatial coordinates of the detected image points as an output signal. In principle, however, the images also can be processed externally.

Figure 8A:
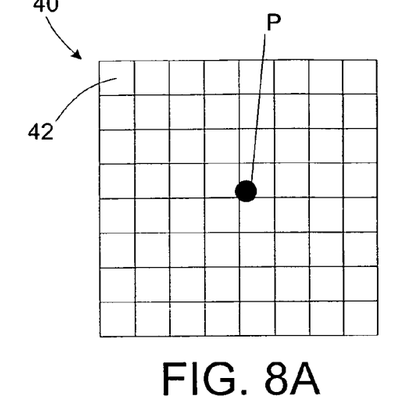
FIGS. 8A-8F illustrate a contrast between ascertaining the position of the image points in the conventional manner and using light scattering effects in accordance with an embodiment of the invention.
Figure 8B:
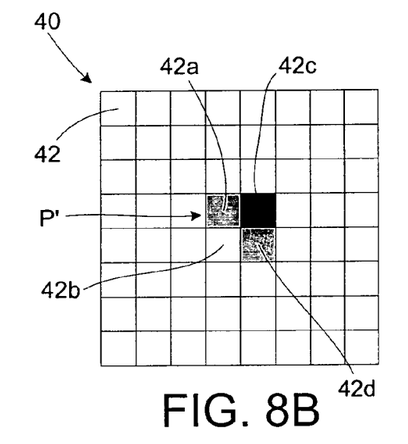
Figure 8C:
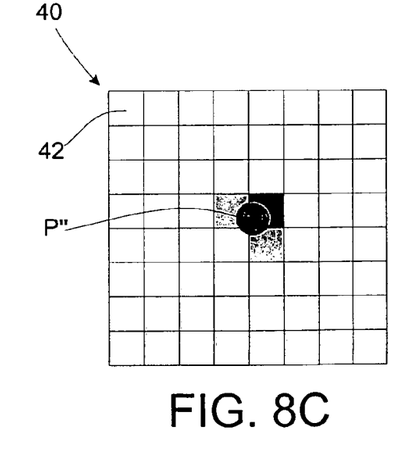

Conventional systems, which use camera systems having a predetermined image resolution, have the disadvantage that their position determining accuracy is substantially dependent on the resolution of the image generating devices. If relatively small markers or landmarks are to be recorded and their position determined, or in the case of markers and landmarks that are relatively far from the image generating device, the accuracy of conventional image generating devices quickly reaches its limits. An example of such an image generating device can be seen in FIGS. 8A-8C. FIGS. 8A-8C show how an image point P would be positionally detected on an 8×8 sensor 40 having sixty-four pixels 42 of a conventional image generating device. It is noted that the size of the image points (e.g., of a marker) on the sensor 40 can be much smaller than the pixel size of the sensor 40, which in this conventional scenario results in a maximum positional accuracy of one pixel 42.

Further, FIGS. 8A-8C illustrate that if the image point P spans four pixels 42a, 42b, 42c, 42d of the sensor 40 and therefore exposes four pixels with different intensities in its projection P'. Interpolating the "brightness" (e.g., the developing or illuminating intensity) of the group of pixels results in a sub-pixel resolution which ascertains a "focus" of the projection P' roughly in the area of the actual image point P. Thus, the position of the point P is calculated to be approximately at the point P'' of FIG. 8C.

As already noted above, such sub-pixel resolution may only be possible when the image point P actually exposes more than just one pixel. In the worst case scenario where the image point P is within a single pixel, the image point position can only be determined as being within the pixel. In the case of small markers or image points (e.g., markers or image points having a size substantially less than one pixel), a significant error can arise.

Thus, the accuracy of the system is determined by the resolution of the sensor 40 and the dynamics and linearity of the sensor pixel 42 (and, in the 3D scenario, by the homogeneity of the marker). In the case of medical tracking systems or other tracking systems, which in many cases depend on accuracies of fractions of millimeters, an accuracy error of the size of one pixel is undesirable. Hence, attempts are constantly made to make markers as large as possible in order to determine the position by averaging a number of exposed pixels.

In other words, the size of markers and their maximum distance from the image generating device are determined by the resolution and the reproduction scale of the lenses. While the size of image points could be increased, then using larger markers would incur significant disadvantages, e.g., handling, cost and weight of the markers.

Furthermore, a few other preconditions should be fulfilled for determining the position of such image points. These preconditions include:

exposing the pixels is only triggered by a single object. Otherwise, the weighting of the grey scales for the sub-pixel resolution will be incorrect;

the focus is the interpolated center for the brightness (this is not the case if a marker is partially hidden, is not round or is tarnished, or if the reflecting surface is not projected with a uniform brightness);

a round marker produces the same image on two sensors if viewed from two different angles (this is likewise not the case if the marker is not round, is tarnished or partially hidden, or if the brightness of the reflecting surface is not homogenous);

the image of the marker is large enough to cover at least one pixel (in practice, at least four); and/or the marker is bright enough to be distinguishable from background noise.

All of these assumptions and restrictions incur disadvantages for conventional tracking systems. Attempts have been made to solve the problems by using image generating devices with ever higher resolutions. However, very high-resolution image sensors can be very expensive and, therefore, significantly increase costs. Also, some of the problems cited above cannot simply be solved by using exceedingly high-resolution image generating devices (e.g., when image points are not completely visible, such as tarnished markers). Another disadvantage is that higher-resolution sensors usually have a significantly smaller pixel area and therefore can be less sensitive, which can result in potentially long exposure times. This can be problematic when objects are moving.

The developers of tracking systems thus find themselves in a sort of "Catch 22"; on the one hand, the markers should not be arbitrarily enlarged, and on the other hand, the resolution should not be arbitrarily increased.

This problem can be solved by an image generating device for an optical tracking system, such as a medical tracking system, wherein the position of a recorded image point is determined, the image point including a light scattering effect generating means. Thus, instead of enlarging the markers or increasing the resolution, the light scattering effect generating means creates a "fuzzy" image. Through the directed, defined scattering of the light of a marker, it is possible to expose a greater number of pixels on a sensor of the image generating device, thus providing a spatially larger amount of information on the image sensor. When light scattering effects are generated, brightness gradients are created (e.g., the location of the brightest point of the image point at its actual location, and the brightness abates with distance). This provides a gradient which can be used to ascertain the exact position of the image point.

Thus, determining the location of the image point can be made more exact, even though the image as a whole can be made fuzzier by the light scattering effect.

Using such an image generating device, it therefore is possible to use an image recording system having a relatively low resolution. The markers no longer need to be large, and can be very small, provided they emit or reflect a sufficient brightness to create determinable image points and scattering patterns. This forsakes the demands on the sharpness of the image in exchange for image points that are easier to detect. The information on the actual position of the image point is achieved by optimally combining the image resolution and dynamics (sensitivity) of the sensor and the quality of the scattering pattern. If known and specific light scattering effects are used, the total energy detected from the image point is distributed over a number of pixels in a known pattern and at known angles.

An example of the distribution latterly cited above is realized in a preferred embodiment in which the light scattering effect generating means is a star and/or cross effect generating means that generates star and/or cross effects in two directions at a predetermined angle. Preferably, the angle between stars and/or cross patterns is about 90 degrees.

Higher-order star and/or cross effects also can be generated. For example, star and/or cross effects in at least three directions having a predetermined angle with respect to each other, such as, for example, an angle of 180 degrees divided by the number of directions, e.g., at identical angular distances.

With the above embodiments, a particular advantage arises as compared to targeted, diffuse defocusing. More specifically, by configuring the light scattering effect generating means, it is possible to predetermine the angles at which the cross and/or star pattern are going to be generated. With such prior known directions, it is much simpler to detect and ascertain the intersection points and therefore the image points themselves, since only the brightest arrangement parallel to the star beams (which form a line of the "cross-hairs") are ascertained. The projection of the image point, e.g., the marker, is then situated at the intersection point.

It should be noted that star and/or cross effect generating means are not the only conceivable light scattering effect generating means. It would be likewise conceivable, for example, to use many and various types of soft-focus effects in order to scatter the brightness of image points uniformly and homogeneously outwards, wherein the brightness decreases gradually.

The light scattering effect generating means can assume various embodiments. A hardware configuration, for example, would be a light scattering effect filter, in particular a star and/or cross effect filter, which is arranged in front of, behind, on or in a camera lens system.

Furthermore, an optical tracking system, such as a medical tracking system or the like, can be provided with an image generating device such as has been described above. In accordance with one embodiment, such a tracking system can include an image processing unit that ascertains a position of an image point on the basis of the light scattering pattern, in particular on the basis of the star effect lines and/or their intersection points.

In accordance with another embodiment, such a tracking system includes an image generating device having at least two spaced cameras, and an image processing unit that ascertains the two-dimensional position of an image point in the image of each camera on the basis of the light scattering pattern, in particular the star effect lines and/or their intersection points, and calculates a spatial position of the image point from the ascertained two-dimensional positions.

Furthermore, a method is also disclosed, for determining the position of a recorded image point by means of an optical tracking system, such as a medical tracking system, in which an image is generated using an image generating device, and a light scattering effect, in particular a star and/or cross effect, is generated on the image for predetermined image points. The position of an image point is ascertained on the basis of the light scattering pattern projected on the image, in particular on the basis of the star and/or cross effect lines and/or their intersection points.

There then exists the possibility of determining the position of the image point by taking into account the prior known and predetermined angles of star and/or cross effect lines with respect to each other. The star and/or cross effects can be generated in two directions that are at a predetermined angle with respect to each other, preferably an angle of about 90 degrees. However, there also exists the possibility of generating the effects in three or more directions that are at a predetermined angle with respect to each other, preferably an angle of 180 degrees divided by the number of directions.

In one embodiment, the star and/or cross effects are generated in at least a number of directions that exceeds the number of image points to be positionally ascertained by one. Using this configuration, an image point can be reliably ascertained at the point where the highest number of effect lines intersect.

The position of the image point additionally can be ascertained on the basis of the brightness gradient of the light scattering pattern, such as the star and/or cross effect lines, since the greatest projected brightness will be at the point where the image point is projected.

A particular application is in the field of image-guided, navigation-assisted medical treatment in which the position of a patient or a medical instrument and/or medical treatment apparatus is detected with the aid of markers and with the aid of a camera system (tracking system), in order to be able to perform image-assisted surgery.

The invention has numerous advantages, including lower overall system costs, extremely small and light markers, simplified marker detecting procedures, increased accuracy, and/or robust/reliable marker detection.

Light scattering effects such as, for example, star and/or cross effects, are shown in FIGS. 5A-5B and 6A-6B. The two contrasted images in FIGS. 5A-5B and 6A-6B show the effect of a star and/or cross filter in an image with a number of bright image points (spotlights). As can be seen, using such an effect on the spotlights results in a cross pattern (FIG. 5B) or a star pattern (FIG. 6B), depending on the effect arrangement. The intersection point of the perpendicular beams (FIG. 5B) is the center of the image point, e.g., the spotlight, and is the brightest point. Uncertainties about potential positions of image points could be caused by beams of different image points intersecting and, therefore, a number of intersection points arise. This problem can be solved based on the brightness or brightness gradient of the beams, or by incorporating information on the beam shape and using higher-order star and/or cross filters, as shown, for example, in FIG. 6B.

Figure 9:
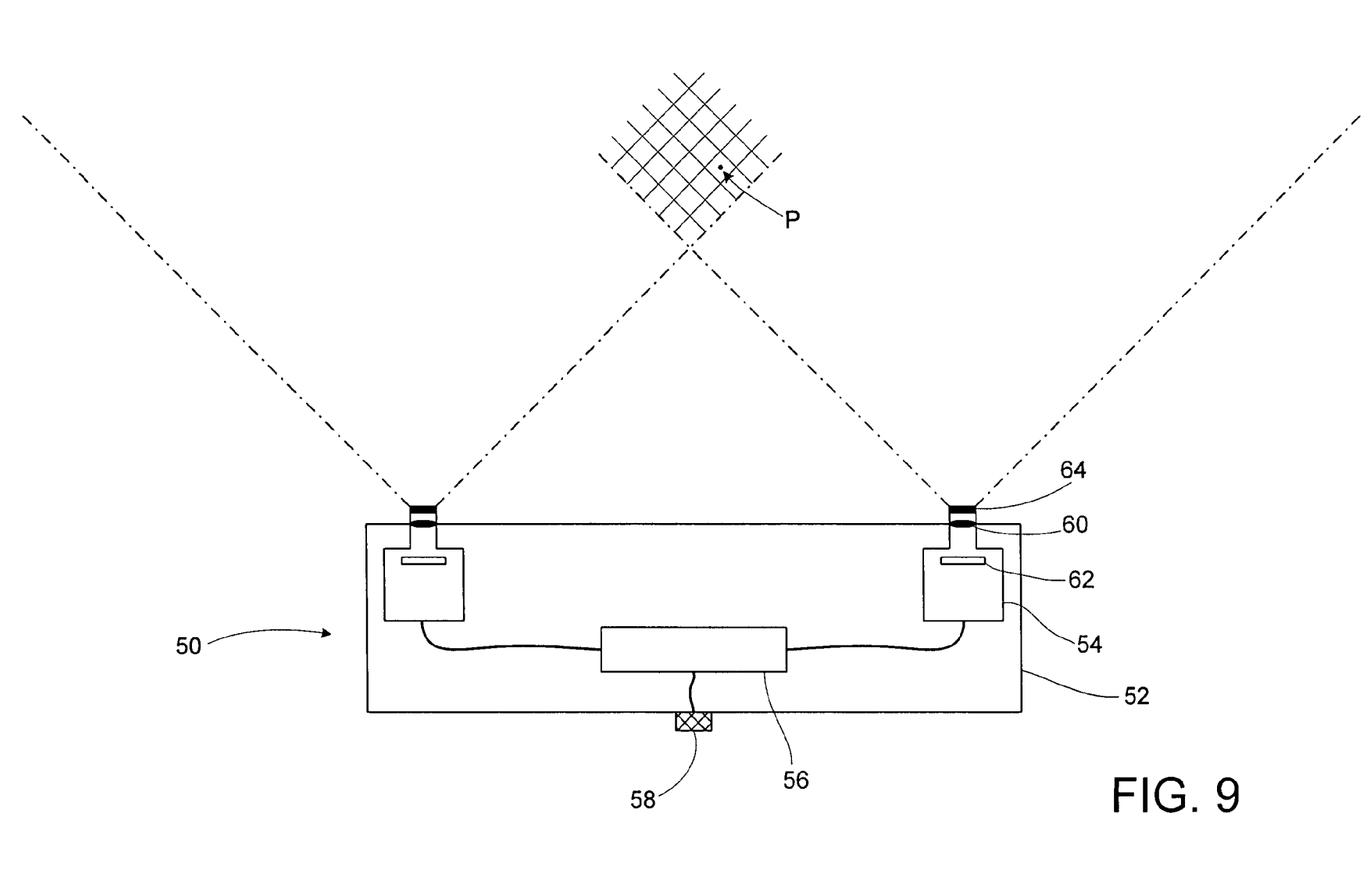
FIG. 9 is a schematic representation of an optical tracking system.

The star and/or cross effect can be achieved in various ways, as already described above. One example is that of using a star or cross filter as shown in FIG. 9. FIG. 9 shows the schematic representation of a medical tracking system 50. The system 50 includes a casing 52 that is fitted with two cameras 54. Each part in FIG. 9 is only provided with a reference numeral once, even if, as with the cameras, two are provided.

The cameras 54 exhibit a common visual range indicated by crosshatching, and the tracking system 50, when it is calibrated, can ascertain the three-dimensional position of an image point within a predetermined coordinate system when the image point is within the common visual range. To this end, the two cameras 54 relay the two-dimensionally ascertained position of each camera to an image processing unit 56 that ascertains a three-dimensional position from the two pieces of information and outputs said three-dimensional position via the output 58. A medical navigation system, for example, can be connected to the output 58, which then enables image-guided surgery if markers on the patient, instruments and/or medical apparatus are positionally ascertained using the tracking system 50.

In the present embodiment, the cameras 54 each include a lens 60 that lies in front of an image sensor 62. A star and/or cross filter is externally positioned in front of the lens 60 and has the reference numeral 64. Thus, using such a camera system, the image point, for example, the indicated image point P, can be positionally ascertained. In order to optimize the construction, the star and/or cross filter can be placed directly onto the lens system using suitable surface finishing techniques, or can be situated in another mold in and/or behind the lens system.

Figure 8D:
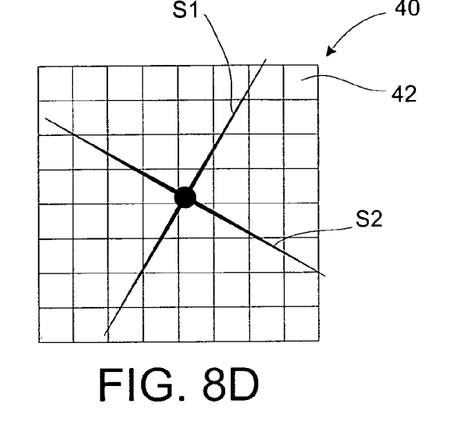
Figure 8E:
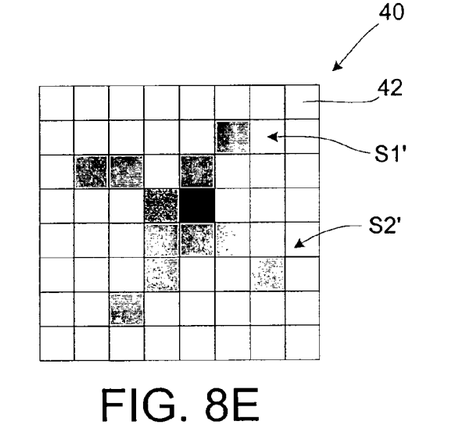
Figure 8F:
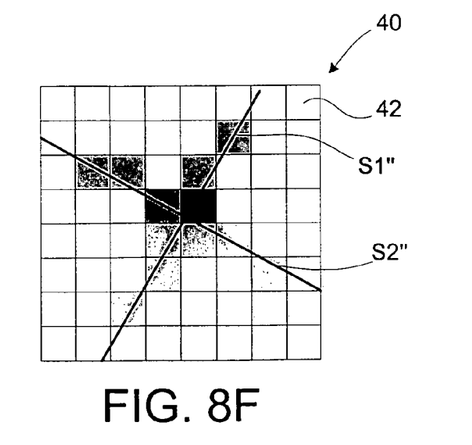

The difficulties that arise when conventionally determining the position of image points have already been described above with respect to the three images of FIGS. 8A-8C. FIGS. 8D-8F show the effect of a 4× star filter when determining the position of the same image point P, for example a marker, wherein beams S1 and S2 are generated by the star and/or cross filter and are initially projected on the sensor as a number of pixel exposures S1', S2'. A much greater number of pixels are then exposed on the sensor, and the beams S1" and S2" can in turn be ascertained from the different brightness with a much higher accuracy, the intersection point of the beams S1" and S2" exactly reproducing the position of the marker or image point.

Specifically, it is clear that interpolating the position of the beams S1, S2, based on the brightness of the associated pixels 42 provides a much more precise estimation of the focus of the object. This is based on the fact that the orientation of the beams is known to be straight (and in this case, perpendicular to each other). Additionally, the direction of the beams is known, since beam direction is defined by the configuration of the star and/or cross filter. Object detection (segmenting) therefore can be simplified by searching for intersection points of straight lines in which the angle of the lines is already known from configuration pre-sets. The total brightness of the marker can be distributed over a number of pixels 42, and in the present case results in a geometric pattern, wherein the intersection point of the straight lines is the center of the marker. The image of the marker could be appreciably smaller than the size of one pixel 42, since the lens distributes the beam over a number of pixels 42.

Advantageously, the procedure no longer relies on algorithms that have to detect a marker outline and find the center point from this information. Further, the edges no longer have to be detected precisely, since the center point of the marker can be calculated based on the actual brightness gradients, the shape of the exposed pixels 42 and a from the geometric intersection point information of the beams.

Based on this procedure, the size of the marker can be appreciably reduced, such that a marker can practically become a point with a negligible size, provided the marker emits or reflects a sufficient brightness. The problem of non-uniformly illuminated, tarnished or covered markers is thus substantially eliminated.

The procedure can be based on one or more of the following assumptions:

the light source that generates the star and/or cross pattern is bright. In practice, the light source can emit or reflect infrared or UV light, such that it does not irritate the user and normal light does not disrupt detection;

the light source which generates the star and/or cross pattern can be small, such that the focus is definitively the brightness center point;

covering, wetting or tarnishing the marker and/or size tolerances are negligible, since the marker is very small with respect to such potential disruptions. If a marker is covered, it is preferable if it provides no image point rather than an incorrect image point. The missing image point can be provided by another (redundant) marker, for example;

the image of the marker can be very small, as long as it is bright enough to generate a cross pattern including a number of pixels.

The assumptions cited above are much less important than the assumptions mentioned previously for detecting the position of image points conventionally (calculating the focus), wherein the shape of the marker is highly relevant.

Figure 7A:
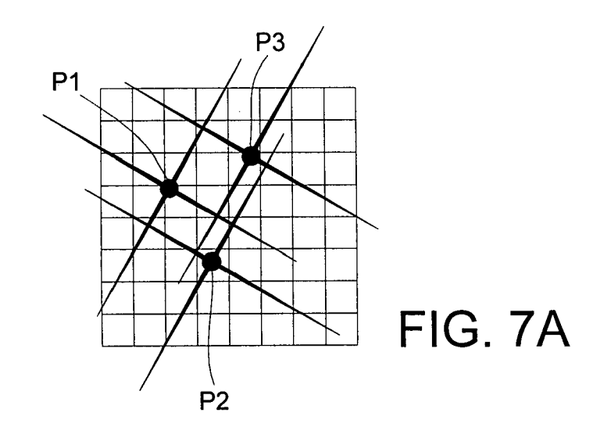
FIG. 7A-7D illustrates examples of determining image points on camera sensors with the aid of star and/or cross effects.
Figure 7B:
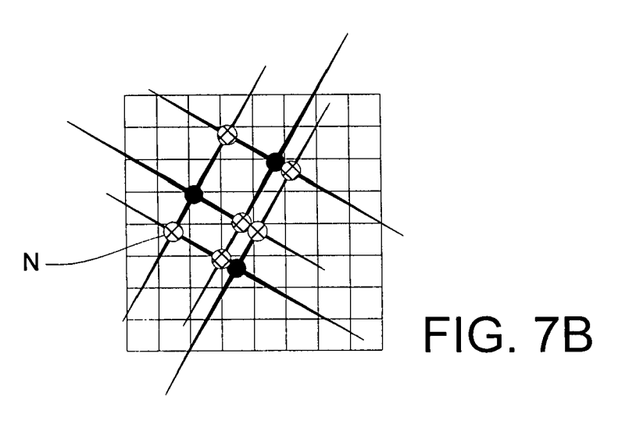

A type of excluding method has already been mentioned above, which prevents incorrect image points from being identified. Such an excluding method is shown again in FIGS. 7A-7D. FIG. 7A shows the correctly identified image points P1, P2 and P3 at particular intersection points of a number of light beams. FIG. 7B, however, shows that if only the intersection points are considered, a number of points would actually result, one of which is indicated as a false image point N. The false image points are indicated by crosshatching.

Figure 7C:
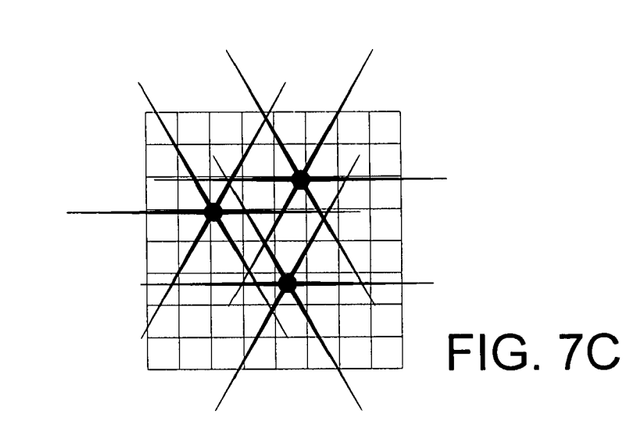

This situation could be corrected by using higher-order star and/or cross filters, as for example in the image in FIG. 7C.

Using this measure, an image point can be identified only at the points where three beams intersect.

Figure 7D:
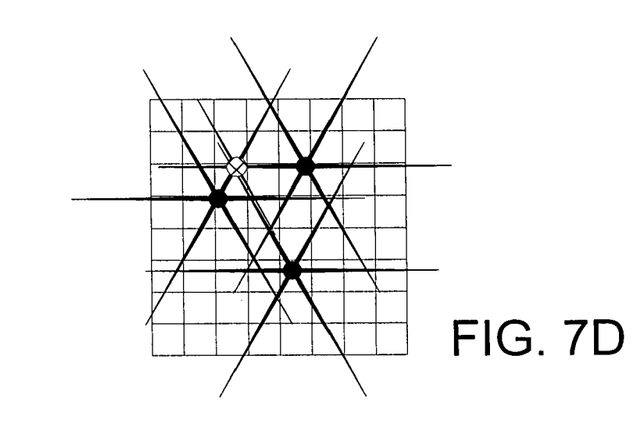

In this case there still exists the possibility that uncertainties remain. Thus, FIG. 7D shows that the point N is likewise the intersection point of three beams, even though it does not actually represent an image point. In such cases, it is useful to adduce the brightness of the point N as a whole. Because the beams decrease in brightness from the center outwards, the point N will not exhibit the same degree of brightness as the actual image points, and it can thus be excluded. Another indication of a correct marker is the fact that the beams S1 and S2 always have the same brightness at the intersection point, as shown in FIGS. 8D-8F. This criterion is not fulfilled by the points N in FIGS. 7A-7D. The order of exclusion can be:

1st intersection point, 2nd intersection point of the order of the star and/or cross filter, 3rd intersection point having the highest brightness, and 4th intersection point having the same brightness as the beams.

Thus, in each case, the correct image points P1, P2 and P3 can be ascertained.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A positional marker system trackable by an optical tracking system having a sensor with a predetermined pixel size, comprising:

at least one of a light-emitting and light-reflecting marker that can be positionally detected by the sensor of the optical tracking system, said at least one of the light-emitting and light-reflecting marker formed as a point light, said point light dimensioned such that an image of the point light detected by the sensor is smaller in size than the predetermined pixel size of the sensor, wherein the optical tracking system is a medical tracking system.

2. The positional marker system as set forth in claim 1, wherein the point light emits a homogeneous light in an emitting direction.

3. The positional marker system as set forth in claim 1, wherein the point light is a point light source and/or a point light reflector.

4. The positional marker system as set forth in claim 1, wherein the point light has a minimum size of about 30 micrometers.

5. The positional marker system as set forth in claim 1, wherein the point light has a minimum size of about 50 micrometers.

6. The positional marker system as set forth in claim 1, wherein the point light has a minimum size of about 62.5 micrometers.

7. The positional marker system as set forth in claim 1, wherein the point light is processed or formed such that the point light emits light in a spatially uniform distribution.

8. The positional marker system as set forth in claim 1, wherein the point light comprises an end of a photoconductive inner part of an optical fiber that has been polished or burnished such that the point light forms a convex scattering lens.

9. The positional marker system as set forth in claim 8, wherein the point light is a number of point lights that are the ends of the optical fibers fed from a common light source, wherein the light source can be an actively emitting source or a light collecting device that collects ambient light.

10. The positional marker system as set forth in claim 1, wherein the marker or markers are reflective markers manufactured from a material that exhibits a refraction index of up to about 2.4 or 2.6.

11. The positional marker system as set forth in claim 10, wherein the material is diamond, rutile, fabulite or moissanite material.

12. The positional marker system as set forth in claim 1, wherein the marker or markers are reflective markers made of a transparent or semi-transparent material and exhibit a crystal cut or diamond cut.

13. The positional marker system as set forth in claim 12, wherein the cut is an ideal cut.

* * * * *